United States Patent [19]

Modir

[11] Patent Number: 4,769,036
[45] Date of Patent: Sep. 6, 1988

[54] RECONSTRUCTIVE MAMMARY PROSTHESIS

[76] Inventor: Jamal Modir, 19241 Montara Dr., Los Gatos, Calif. 95030

[21] Appl. No.: 755,930

[22] Filed: Jul. 17, 1985

[51] Int. Cl.$^4$ .............................................. A61F 2/12
[52] U.S. Cl. .......................................... 623/8; 623/11
[58] Field of Search ................................ 623/7, 8, 16; 128/DIG. 21, 1 R

[56] References Cited

U.S. PATENT DOCUMENTS 3,902,198 9/1975 Rathjen .................................... 623/8

FOREIGN PATENT DOCUMENTS 2419065 11/1979 France .................................... 623/16
2093701 9/1982 United Kingdom .................. 623/16

OTHER PUBLICATIONS

H. Zarem, "Silastic Implants in Plast. Surg.", The Bulletin, vol. 10, No. 2, Dow Corning, Apr. 1968.
McGhan, "Silicone Block", Catalog, Feb. 1977.
Surgitek, "Implantable Silicone Plastigel", Feb. 1980, Med. Engineering Corp.

Primary Examiner—Richard J. Apley
Assistant Examiner—David J. Isabella
Attorney, Agent, or Firm—Flehr, Hohbach, Test, Albritton & Herbert

[57] ABSTRACT

A reconstructive mammary prosthesis encompasses an annular section of the breast and may be provided with suture tabs and/or a thin microfiber layer for facilitating anchoring to the adjacent tissue and contour retention.

4 Claims, 1 Drawing Sheet

RECONSTRUCTIVE MAMMARY PROSTHESIS

BACKGROUND OF THE INVENTION

The present invention relates to a subcutaneous-intramammary prosthesis and, in particular, to a mammary prosthesis designed to replace an annular section or quadrant of breast tissue after its resection for any pathological reason, such as, for example, partial mastectomy.

The mammary or breast prostheses which have been used in the past include external, brassiere-type prostheses which are believed to have been used when the breast has been amputated, and internal or subcutaneous prostheses. Subcutaneous mammary prostheses are used for breast augmentation, that is, to enhance the existing contour of healthy breast tissue, or for reconstruction, to restore and/or enhance the breast contour when abnormal, diseased or damaged tissue has been removed by surgery.

The breast augmentation prostheses which are known to me are typified by the silicone gel-filled, pad shaped flexible container which is disclosed in Rathjen, U.S. Pat. No. 3,902,198, issued Sept. 2, 1975. Rathjen also discloses the use of porous fixation loops, which are attached to the posterior wall of the pad, and are invaded by body tissue to fix or anchor the prosthesis to the chest wall. In addition, Rathjen suggests the optional use of absorbable sutures to temporarily hold the implant in place until the anchoring or fixation is complete.

The only subcutaneous reconstructive prostheses which are known to me are those which are used to totally reconstruct or replace the breast after radical mastectomies. As is well-known to those who are familiar with breast surgery and the technology of the devices used in reconstructive surgery, reconstructive prostheses must possess the characteristics of softness and resiliency. At the same time, reconstructive prostheses must have sufficient rigidity for shape retention. In addition, it is desirable to provide fixation so that the device will retain its position without shifting during normal body movement.

Cronin, U.S. Pat. No. 3,293,663, issued Dec. 27, 1966, apparently typifies the silicone gel-filled, shaped, flexible containers which provide a soft, resilient, reconstructive human breast replacement. However, various attempts have been made to improve upon the shape retention capabilities of the basic gel-filled, flexible mammary prosthesis. For example, one approach for enhancing shape retention involves dividing the prosthesis internally into separate compartments. See Pangman, U.S. Pat. No. 3,559,214, issued Feb. 2, 1971. Also, Hamas, U.S. Pat. No. 4,264,990, issued May 5, 1981, uses a rigidizable backing structure which is attached to the posterior of the prosthesis to alleviate deformation caused by scar tissue contracture. Redinger, U.S. Pat. No. 4,455,691, issued June 26, 1984, uses a composite silicone elastomer container to decrease the outmigration of silicone gel.

In addition to the attempts to provide softness and resiliency in conjunction with shape retention, the art evidences attempts to fix reconstructive prostheses by attaching a porous fabric to the posterior of the prosthesis so that invasion by body tissue anchors the prosthesis to the chest wall. This approach is described in the Cronin patent. In addition, the Pangman patent discloses the use of an outer foam covering which completely surrounds the prosthesis. The covering allows the in-growth of tissue to anchor the prosthesis, and, because of the covering's small thickness, limits the in-growth of the tissue and presumably reduces shrinkage and hardening due to encapsulation by scar tissue.

SUMMARY OF THE INVENTION

It is an object of the present invention to provide an intramammary or subcutaneous reconstructive prosthesis which is designed for reconstructive mammaplasty where the breast tissue has been *partially* removed rather than totally removed or amputated.

It is another, more specific object of the present invention to provide a mammary prosthesis for subcutaneous and/or intramammary implantation of a section or quadrant of the breast which provides softness and resiliency, along with shape retention.

It is another object of the present invention to provide a mammary prosthesis for subcutaneous implantation which corresponds to an annular section of the breast and which is adapted for being anchored in place.

In one aspect, the subcutaneous mammary prosthesis of the present invention comprises a flexible body which is shaped as an annular section or quadrant of the breast and extends from the posterior portion of the breast to the anterior portion. In cross section, the prosthesis defines a generally wedge shape having two substantially straight inner sides and a curved outer side which approximates the outer contour of the breast. Suture tabs can be formed or otherwise attached to the inner sides of the body to permit fixation to the breast tissue and the overlying skin.

In another aspect, the present invention is a reconstructive mammary soft tissue replacement prosthesis comprising a seamless flexible silicone envelope which defines an annular section of the breast from the posterior portion or chest wall to the anterior portion and is filled with a cohesive silicone gel. In cross section, the filled envelope defines a wedge shape having two substantially straight inner sides, and a curved outer side which corresponds substantially to the contour of the breast. The envelope is covered with a thin microfiber polyurethane layer for invasive fixation to the surrounding breast tissue. In addition, suture tabs are formed on the envelope and provide temporary fixation during the period of tissue in-growth, or permanent fixation. Such suture tabs could be made from an absorbable material.

The above and other aspects of my invention are described with respect to the drawings, in which.

DETAILED DESCRIPTION OF THE INVENTION

Figure 1:
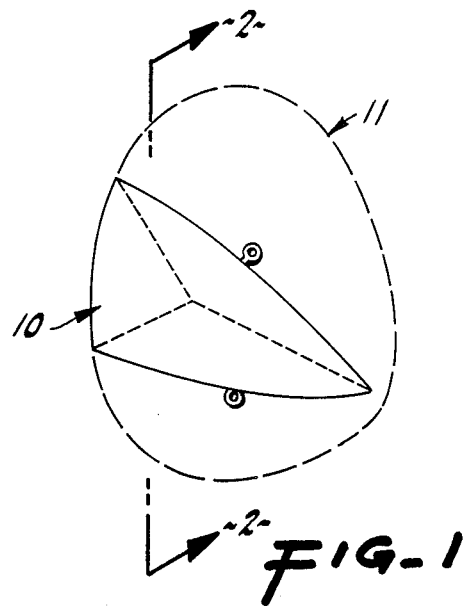
FIG. 1 is a perspective view showing the quad reconstructive mammary prosthesis of my present invention relative to the shape of the human breast and the total replacement prostheses which are conventionally used.

FIG. 1 is a perspective view, partially in phantom, which illustrates the soft tissue replacement prosthesis 10 of the present invention with respect to the human breast, which is schematically represented at 11. The figure is also designed to illustrate the size and shape of the "quadrant" or "quad" prosthesis 10 relative to the conventional reconstructive mammary prothesis, which is designed to replace the entire breast. The conventional prosthesis is thus also represented by the shape 11. The quad reconstructive mammary prosthesis 10 is designed to take advantage of the recent trend towards partial breast resectioning, that is, the trend toward removing only a minimal amount of diseased or damaged tissue, rather than the massive prophylatic tissue removal which was previously in vogue. The configuration of my quad mammary reconstructive prosthesis 10 is designed to take advantage of this minimal approach to tissue removal and involves the use of an annular cross-sectional configuration (see, for example, FIG. 3) which involves a much smaller replacement volume than conventional prosthesis 11.

The advantage of this reduced volume is two-fold. First, the smaller volume and weight provide inherently better shape retention for a given degree of softness and resiliency than do conventional breast replacement prostheses 11. Secondly, the sectioned prosthesis construction closely conforms to and relies upon the remaining, healthy breast tissue for support, both for fixation or anchoring and also for contour retention.

Figure 2:
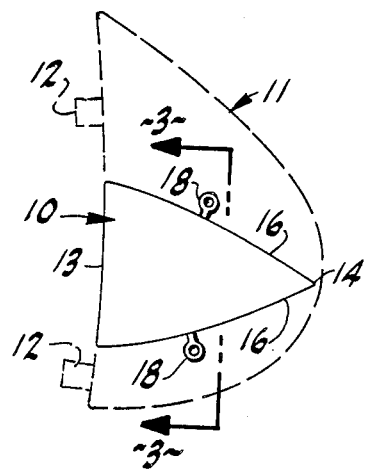
FIG. 2 is a cross-sectional view taken along the line 2—2 in FIG. 1.

In addition, those of skill in the art will understand that the prior art total replacement prosthesis, such as that outlined at 11 in FIGS. 1 and 2, typically can be anchored only to the chest wall. The anchoring means, which is represented in phantom at 12 in FIG. 2, can comprise the porous fabric disclosed in the Cronin patent or the fixation loops disclosed in the Rathjen augmentation prosthesis patent. In contrast, the present quad reconstructive mammary prosthesis 10 is supported and fixed by the healthy breast tissue along its sides 16—16, as shown, for example, in FIG. 2, so that the prosthesis 10 is supported all along its length, from the posterior 13 of the breast at the chest wall to the anterior 14 of the breast at or proximate the nipple, without the need to employ anchoring means at the posterior. In addition, and unlike conventional prostheses, one or more permanent or body-absorbable suture tabs 18—18 can be attached to either or both of the sides 16—16 to temporarily anchor the prosthesis 10 during the healing period, or to aid in permanently anchoring the prosthesis.

Figure 3:
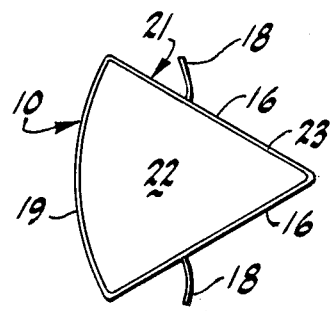
FIG. 3 is a cross-sectional view taken along the line 3—3 in FIG. 2.

The cross-sectional shape and the construction of the quad reconstructive mammary prosthesis 10 of the present invention are clearly illustrated in the cross-sectional view of FIG. 3. As shown, the generally wedge shape of the prosthesis is defined by the two substantially straight internal (subcutaneous) sides 16—16 and the interconnecting, external, generally convex-shaped external side 19. Side 19 is configured to approximate the contour of the replaced breast tissue. While the illustrated sides 16—16 of the annular prosthesis 10 subtend an angle of approximately 60°, it is to be understood that this angle can vary considerably, limited only by the requirement that the size and volume of the prosthesis be relatively small compared to the total volume of the breast, so that the breast can provide the necessary fixation for the prothesis and so that the prosthesis is conformed to the contour and shape of the supporting breast tissue.

Referring further to the cross-sectional view of FIG. 3, in a preferred embodiment the prosthesis is constructed from Silastic medical grade silicone material and includes a seamless silicone envelope or sack 21 which is filled with a cohesive silicone gel material 22 and is coated with a thin microfiber polyurethane layer 23. This construction is known and is of the general type disclosed, for example, in various embodiments and modifications in the above-described Cronin U.S. Pat. No. 3,293,663, Pangman U.S. Pat. No. 3,559,214, Rathjen U.S. Pat. No. 3,902,198, and Redinger U.S. Pat. No. 4,455,691.

These patents are incorporated by reference. The important point regarding this construction is that my prosthesis utilizes the soft, resilient gel-filled, flexible container without the usual problems of shape retention or fixation. In addition, the use of the wedge shape provides a relatively large surface area along the sides 16—16 for supporting the relatively small volume prosthesis 10. This support can be enhanced by the suture tabs 18—18 mentioned above, and in addition, by the porous coating 23 which permits shallow supportive invasion by healthy breast tissue all along the large surface area of the sides 16—16. This is in contrast to the prior art total replacement prostheses, for which the only anchoring site is at the posterior of the device, that is, at the chest wall.

Figure 4:
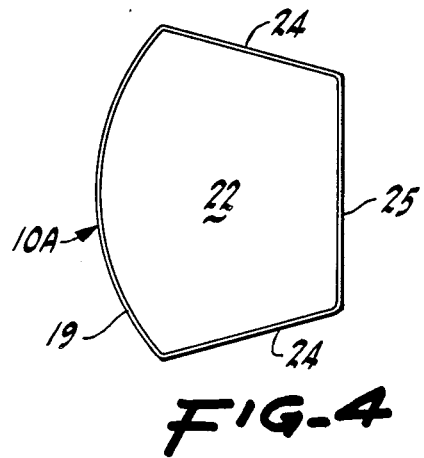
FIG. 4 is a cross-sectional view similar to that shown in FIG. 3 of an alternative prosthesis configuration.

One example of an alternative configuration for my quad reconstructive mammary prosthesis is shown in FIG. 4. There, the prosthesis 10A is configured as substantially a rectangle with outer side 19, inner sides 24—24 and base 25. Of course, other cross-sectional configurations will be derived by those skilled in the art, as needed or as suited to the particular pattern of tissue excision. In addition, the construction will be readily adapted to flexible materials other than the particular materials used in the construction of the gel-filled container. It will also be appreciated that the "outer" side 19 of the quad mammary reconstructive prosthesis 10 may be subcutaneous, either beneath the skin or beneath the skin plus outer tissue, where surgery permits. Finally, it should be pointed out that the term "quad" is used as a convenient identifier of the general shape of my prosthesis and does not limit the prosthesis to a one-quarter cross section or to any other specific size or angular orientation.

Having thus described preferred and alternative embodiments of my quad reconstructive mammary prosthesis, what is claimed is:

1. A mammary prosthesis for subcutaneous implantation comprising: a flexible body designed to extend in length substantially from the posterior of the breast to the anterior thereof and having a transverse cross-section corresponding in shape to a section or quadrant of the breast; the body defining, in transverse cross-section, a wedge shape comprising at least three sides, including two substantially straight supporting inner sides for anchoring the body to adjacent breast tissue and for conforming the shape of the body to the breast, and a curved outer side corresponding to the contour of the breast, and wherein the body comprises a seamless silicone envelope which is filled with a cohesive silicone gel.

2. A reconstructive mammary soft tissue replacement prosthesis comprising: a seamless silicone envelope designed to extend in length substantially from the posterior of the breast to the anterior thereof and having a transverse cross-section corresponding to a generally wedge shaped transverse section of the breast and being filled with a cohesive silicone gel and covered with a thin microfiber polyurethane layer; the transverse cross-section of the envelope comprising at least three sides, including two substantially straight inner sides for anchoring the envelope to adjoining breast tissue and for conforming the envelope to the shape of the breast, and a curved outer side corresponding to the outer contour of the breast; and means for anchoring the envelope to the adjoining breast tissue.

3. The prosthesis of claim 1, further comprising a third inner side between and joining said two inner sides.

4. The prosthesis of claim 2, further comprising a third inner side between and joining said two inner sides.

* * * * *